(12) United States Patent
Borody et al.

(10) Patent No.: US 8,999,360 B2
(45) Date of Patent: Apr. 7, 2015

(54) COMPOSITIONS AND METHODS FOR TREATING EXTRACELLULAR PARASITIC INFECTIONS

(76) Inventors: Thomas Julius Borody, Sydney (AU); Soledad Carsula, Rouse Hill (AU)

( * ) Notice: Subject to any disclaimer, the term of this patent is extended or adjusted under 35 U.S.C. 154(b) by 159 days.

(21) Appl. No.: 13/502,366

(22) PCT Filed: Oct. 22, 2010

(86) PCT No.: PCT/AU2010/001411
§ 371 (c)(1),
(2), (4) Date: May 1, 2012

(87) PCT Pub. No.: WO2011/047439
PCT Pub. Date: Apr. 28, 2011

(65) Prior Publication Data
US 2012/0207826 A1 Aug. 16, 2012

(30) Foreign Application Priority Data
Oct. 22, 2009 (AU) ................................ 2009905150

(51) Int. Cl.
A61K 31/34 (2006.01)
A61K 31/65 (2006.01)
A61K 31/4174 (2006.01)
A61K 31/4178 (2006.01)
A61K 31/4704 (2006.01)

(52) U.S. Cl.
CPC ............. *A61K 31/4174* (2013.01); *A61K 31/65* (2013.01); *A61K 31/4704* (2013.01)

(58) Field of Classification Search
USPC ........... 424/405, 408, 436, 451, 463; 514/4.6, 514/154, 253.08, 254.07, 254.1, 256, 275, 514/374, 376, 378, 380, 385, 386, 396, 398, 514/399, 430, 438, 442, 449, 461, 473; 544/242, 323, 325, 363, 370, 374; 548/192, 230, 234, 246, 330.1, 330.5; 549/473; 564/123, 163, 167, 168, 172
See application file for complete search history.

(56) References Cited

U.S. PATENT DOCUMENTS
6,475,518 B1 11/2002 Baumgart et al.

FOREIGN PATENT DOCUMENTS
AU 2003100568 A4 9/2003
AU 2003100568 A4 * 9/2003 .............. A61K 31/47

OTHER PUBLICATIONS

Divo et al., "Activity of Fluoroquinolone Antibiotics against *Plasmodium falciparum* in Vitro," Aug. 1988; Antimicrobial Agents and Chemotherapy; 32(8):1182-1186.*
El-Masry et al., "Eradication of *Blastocystis hominis* carriage: a comparative retrospective review of four antiprotozoal agents," 1993; Journal of Tropical Medicine; 2(4):9-13; Abstract only.*
Morch et al., "Treatment-ladder and genetic characterization of parasites in refractory giardiasis after an outbreak in Norway," Apr. 2008; Journal of Infection; 56(4):268-273; Abstract only.*
Harold C. Neu, "Synergy and Antagonism of Fluoroquinolones with Other Classes of Antimicrobial Agents", 1993; Drugs; 45 (Suppl. 3):54-58.*
Sugar et al., "Effectiveness of Quinolone Antibiotics in Modulating the Effects of Antifungal Drugs," Nov. 1997; Antimicrobial Agents and Chemotherapy; 41(11):2518-2521.*
Sugar et al., "Combination Antifungal Therapy in Treatment of Murine Pulmonary Mucormycosis: Roles of Quinolones and Azoles," Jul. 2000; Antimicrobial Agents and Chemotherapy; 44(7):2004-2006.*
Borody et al., "Eradication of *Dientamoeba fragilis* can resolve IBS-like symptoms," 2002; Journal of Gastroenterology and Hepatology; 17 Suppl., p. A103, Paper No. 23.*
William A. Petri, Jr., General Review, Nov. 2003; Trends in Parasitology; 19(11):523-526; Abstract only.*
Borody et al., "Eradication of *Dientamoeba fragilis* can resolve IBS-like symptoms", Journal of Gastroenterology and Hepatology (2002) 17 Suppl. A103.
Divo et al., "Activity of Fluoroquinolone Antibiotics against *Plasmodium falciparum* In Vitro", Antimicrobial Agents and Chemotherapy, Aug. 1988, p. 1182-1186 vol. 32, No. 8.
Nakajima et al., "In Vitro and In Vivo Antifungal Activities of DU-6859a, a Fluoroquinolone, in Combination with Amphotericin B and Fluconazole against Pathogenic Fungi", Antimicrobial Agents and Chemotherapy, Jul. 1995, p. 1517-1521 vol. 39, No. 7.
Neu, Harold C., "Synergy and Antagonism of Fluoroquinolones with Other Classes of Antimicrobial Agents", Drugs 45 (Suppl. 3): 54-58, 1993.
Petrou et al., "In-Vitro Activity of Antifungal Agents in Combination with Four Quinolones", Drugs Exptl. Clin. Res. XIV (1) 9-18 (1988).
Rajaa et al., "Activation of phagocytic cell NADPH oxidase by norfioxacin: a potential mechanism to explain its bactericidal action", Journal of Leukocyte Biology, 2002, 71:255.
Rossignol et al., "Effect of Nitazoxanide in Persistent Diarrhea and Enteritis Associated With *Blastocystis hominis*", Clinical Gastroenterology and Hepatology 2005;3:987-991.

(Continued)

*Primary Examiner* — Jane C Oswecki
(74) *Attorney, Agent, or Firm* — Gregory P. Einhorn; Spruson & Ferguson

(57) ABSTRACT

There is disclosed herein a composition for treating extracellular parasitic infections, the composition comprising one or more of the following combinations: at least one quinolone or fluoroquinolone together with at least one tetracycline, iodoquinol, an azole or imidazole; or at least two agents selected from the group consisting of iodoquinol, thiazolidones, tetracycline, nitroimidazoles, cotrimoxazole and diloxanide furoate. There is also disclosed herein a method for treating extracellular parasitic infections in a vertebrate in need of said treatment, wherein said treatment comprises administering to said vertebrate a therapeutically effective amount of (i) a composition comprising a quinolone or fluoroquinolone together with a pharmaceutically acceptable carrier or (ii) a composition of the invention or (iii) a combination of at least one quinolone or fluoroquinolone optionally together with at least one tetracycline, iodoquinol, an azole or imidazole; or (iv) a combination of at least two agents selected from the group consisting of iodoquinol, thiazolidones, tetracycline, nitroimidazoles, cotrimoxazole and diloxanide furoate.

35 Claims, No Drawings

(56) References Cited

OTHER PUBLICATIONS

Shein et al., "Colitis Due to *Dientamoelxz fragilis*", The American Journal of Gastroenterology, vol. 78, No. 10, 1983, pp. 634-636.

Sugar et al., "Effectiveness of Quinolone Antibiotics in Modulating the Effects of Antifungal Drugs", Antimicrobial Agents and Chemotherapy, Nov. 1997, pp. 2518-2521, vol. 41, No. 11.

Sugar et al., "Combination Antifungal Therapy in Treatment of Murine Pulmonary Mucormycosis: Roles of Quinolones and Azoles", Antimicrobial Agents and Chemotherapy, Jul. 2000, pp. 2004-2006, vol. 44, No. 7.

Yakoob et al., "Irritable Bowel Syndrome: In Search of an Etiology: Role of *Blastocystis hominis*", Am. J. Med. Hyg. 70 (4), 2004, pp. 383-385.

* cited by examiner

COMPOSITIONS AND METHODS FOR TREATING EXTRACELLULAR PARASITIC INFECTIONS

This application is a national phase patent utility filing under 35 USC §371, for International (PCT) Patent Application serial no. PCT/AU2010/001411, filed Oct. 22, 2010, which claims benefit of priority to Australian Patent Application Serial No. (USSN) 2009-905150, filed Oct. 22, 2009. The aforementioned applications are expressly incorporated by reference herein in their entirety for all purposes.

TECHNICAL FIELD

The present invention relates to compositions and methods for treating extracellular parasitic infections.

BACKGROUND OF THE INVENTION

Numerous parasites may cause infestation of the gastrointestinal tract in man. Most cases of intestinal parasitisation occur in areas of poor sanitation and particularly in 'third world' countries. With few financial resources for research in third world countries and low market expectations from the development of anti-parasitic therapies by large 'pharma' there has been inadequate market pressure to come up with medications to combat even the most common parasites infesting the gastrointestinal tract. Fortunately, outside the 'third world' there is a number of parasitic infestations which are common in developed countries yet these are poorly addressed, perhaps because anti-parasite drug development has been more the realm of the 'third world'. For example malaria parasites, *Entamoeba histolytica, Shistosomiasis* and similar parasites are rarely detected in developed countries except in incoming visitors to countries such as United States, Australia and regions such as Europe. On the other hand, there has been little recognition by gastroenterologists and general practitioners in developed countries particularly of two parasites common in the developed countries yet poorly addressed and diagnosed with some difficulty. These include various strains of *Blastocystis hominis* and *Dientamoeba fragilis*.

There is emerging compelling literature which suggests that infestation of the bowel flora by parasites can result in symptomatology that is indistinguishable from the very common condition in the west called Irritable Bowel Syndrome (IBS) (Yakoob et al 2004, *Am J Trop Med Hyg* 70: 383; Borody et al 2002, Gastroenterol Hepatol 17: Suppl A103). Irritable Bowel Syndrome is characterized by changes in bowel habit including diarrhoea, constipation, bloating, pain, cramping, urgency and at times nausea. More recently, this condition which was previously thought to be caused by stress and inadequate diet is now increasingly thought to be caused by 'overgrowth of the bowel flora' by infective agents including bacterial agents, and, parasites, many of which are yet to be characterized. Hence, unless one examines the bowel flora in patients with IBS symptoms for common parasites these may be missed and an "IBS" label may be used without giving the patient the opportunity for cure. Such "IBS" then goes on to be misdiagnosed whereas all along it might have been curable by removal of the chronic parasite infection.

In the 'first world' common intestinal parasitic infections include *Blastocystis hominis, Dientamoeba fragilis* and *Giardia lamblia*. These are perhaps the more common parasitic infections of the gut flora, particularly in such countries as the USA, Australia and the UK. Originally *Blastocystis* was not thought to be a pathogenic parasite but more recently has been shown—at least with some sub-types [esp. type 3]—to cause symptoms that can be relieved by treatment. *D. fragilis* is known to be a pathogen albeit it may cause mild symptoms like IBS although and at times colitis has been caused by this parasite. (Skein et al, 1983 Am J Gastroenterol. 78:634).

In this application the inventor identifies the lack of specific first line and second line therapies for these most chronic infections which can cause IBS-like symptoms in developed countries. This situation has left an unmet need and with increasingly more frequent diagnosis of *D. fragilis* and *B. hominis* repeated treatment and failure-to-cure is seen when doctors who do not know how to treat the parasites simply use metronidazole which generally has but a minor effect on parasites. This invention will therefore describe first and second line therapies in patients who have infestation with these common parasites *D. fragilis* or *B. hominis* or both. Single anti-parasitic agents are generally ineffective against these parasites and so combinations are necessary. Furthermore there may be more extended applications to other parasites that may respond to such combinations.

OBJECT OF THE INVENTION

It is an object of the present invention to overcome or substantially ameliorate at least one of the above disadvantages or to provide a suitable alternative.

SUMMARY OF THE INVENTION

According to a first aspect of the present invention, there is provided a composition for treating extracellular parasitic infections, the composition comprising one or more of the following combinations:

at least one quinolone or fluoroquinolone together with at least one tetracycline, iodoquinol, an azole or imidazole; or at least two agents selected from the group consisting of iodoquinol, thiazolidones, tetracycline, nitroimidazoles, cotrimoxazole and diloxanide furoate.

According to a second aspect of the present invention, there is provided use of at least one quinolone or fluoroquinolone optionally together with at least one tetracycline, iodoquinol, an azole or imidazole; or at least two agents selected from the group consisting of iodoquinol, thiazolidones, tetracycline, nitroimidazoles, cotrimoxazole and diloxanide furoate for the manufacture of a medicament for treating extracellular parasitic infections.

According to a third aspect of the present invention there is provided herein a method for treating extracellular parasitic infections in a vertebrate in need of said treatment, wherein said treatment comprises administering to said vertebrate a therapeutically effective amount of (i) a composition comprising a quinolone or fluoroquinolone together with a pharmaceutically acceptable carrier or (ii) a composition of the invention, or (iii) a combination of at least one quinolone or fluoroquinolone optionally together with at least one tetracycline, iodoquinol, an azole or imidazole; or (iv) a combination of at least two agents selected from the group consisting of iodoquinol, thiazolidones, tetracycline, nitroimidazoles, cotrimoxazole and diloxanide furoate.

DEFINITIONS

The following definitions are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer, or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

All the references cited in this application are specifically incorporated by reference are incorporated herein in their entirety. Inclusion herein of any given reference is not intended to indicate that the reference is generally known in Australia or elsewhere.

DETAILED DESCRIPTION OF THE PREFERRED EMBODIMENTS

There is disclosed herein a composition for treating extracellular parasitic infections, the composition comprising one or more of the following combinations:

at least one quinolone or fluoroquinolone together with at least one tetracycline, iodoquinol, an azole or imidazole; or at least two agents selected from the group consisting of iodoquinol, thiazolidones, tetracycline, nitroimidazoles, cotrimoxazole and diloxanide furoate.

There is also disclosed herein use of at least one quinolone or fluoroquinolone together with at least one tetracycline, iodoquinol, an azole or imidazole; or at least two agents selected from the group consisting of iodoquinol, thiazolidones, tetracycline, nitroimidazoles, cotrimoxazole and diloxanide fitroate but excluding the double combination iodoquinol and doxycycline for the manufacture of a medicament for treating extracellular parasitic infections.

In one embodiment, the quinolone or fluoroquinolone is one or more compounds selected from the group consisting of cinoxacin, flumequine, oxolinic acid, piromidic acid, ciprofloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin mesilate, sparfloxacin, temafloxacin, tosufloxacin, clinafloxacin, gemifloxacin, moxifloxacin, gatifloxacin, sitafloxacin, trovafloxacin, ecinofloxacin, and prulifloxacin.

In one embodiment, the tetracycline is tetracycline, chlortetracycline, oxytetracycline, demeclocycline, doxycycline, lymecycline, meclocycline, minocycline, methacycline, rolitetracycline and penimepicycline.

In one embodiment the azole or imidazole is selected from ketoconazole, fluconazole, miconazole, clotrimazole, tioconazole, sulconazole, econazole, itraconazole and mixtures thereof.

In one embodiment the composition further comprises an additional anti-parasitic drug. In one embodiment, the anti-parasitic drug is selected from emetine, quinacrine, satranidazole, flunidazole, ronidazole and mixtures thereof.

In one embodiment, the thiazolidone is selected from the group consisting of nitazoxanide, denitrozoxanide, tizoxanide and mixtures thereof.

In one embodiment, the nitroimidazole is selected from metronidazole, etronidazole, secnidazole, tinidazole, ornidazole, furazolidone and mixtures thereof.

In one embodiment, the composition includes combinations of three or four different agents.

In one embodiment, the composition includes the combination norfloxacin and ketoconazole.

In one embodiment, the composition includes the combination nitazoxanide, furzolidone and secnidazole.

In one embodiment, the composition includes the combination iodoquinol, forazolidone and nitazoxanide.

In one embodiment, The composition includes the combination includes diloxanide furoate, doxycycline and metronidazole.

In one embodiment, the composition includes the combination secnidazole, diloxanide furoate and cotrinoxazole.

In one embodiment, the composition includes the combination metronidazole, nitazoxanide and furazolidone.

In one embodiment, the composition includes the combination cotrimoxazole, diloxanide furoate, secnidazole and doxycycline.

In one embodiment, the composition includes the combination nitazoxanide, furazolidone, secnidazole and doxycycline.

In one embodiment, the composition includes two agents selected from iodoquinol and doxycycline, nitazoxanide and doxycycline, nitazoxanide and secnidazole, furazolidone and secnidazole, furazolidone and nitazoxanide, doxycycline and secnidazole and doxycycline and furazolidone and mixtures thereof.

As required, the composition may include a suitably pharmaceutically acceptable carrier.

There is also disclosed herein a method for treating extracellular parasitic infections in a vertebrate in need of said treatment, wherein said treatment comprises administering to said vertebrate a therapeutically effective amount of (i) a composition comprising a quinolone or fluoroquinolone together with a pharmaceutically acceptable carrier or (ii) a composition of the invention, or (iii) a combination of at least one quinolone or fluoroquinolone optionally together with, at least one tetracycline, iodoquinol, an azole or imidazole; or (iv) a combination of at least two agents selected from the group consisting of iodoquinol, thiazolidones, tetracycline, nitroimidazoles, cotrimoxazole and diloxanide furoate.

In one embodiment, the agents can be administered simultaneously. In another embodiment, the agents can be administered separately in any order. The agents administered separately may be any of the combinations referred to above. For example the combination norfloxacin and ketoconazole; the combination nitazoxanide, furzolidone and secnidazole; the combination iodoquinol, furazolidone and nitazoxanide; the combination diloxanide furoate, doxycycline and metronidazole; the combination secnidazole, diloxanide furoate and cotrimoxazole; the combination metronidazole, nitazoxanide and furazolidone; the combination cotrimoxazole, diloxanide furoate, secnidazole and doxycycline; the combination nitazoxanide, furazolidone, secnidazole and doxycycline; the combinations iodoquinol and doxycycline, nitazoxanide and doxycycline, nitazoxanide and secnidazole, furazolidone and secnidazole, furazolidone and nitazoxanide, doxycycline and secnidazole and doxycycline and furazolidone.

In one embodiment, the extracellular parasite is *Blastocystis hominis, Dientamoeba fragilis* or both.

In one embodiment, the method includes administering a dosage of at least one milligram to five grams per day.

In one embodiment, the quinolone or fluoroquinolone used is norfloxacin.

In one embodiment, the present invention relates to compositions and methods for treating extracellular parasitic infections in vertebrates in need of such treatment for example where the host is infested with either *Blastocystis hominis, Dientamoeba fragilis* or both. It may also be applicable to other infestations, especially *Giardia lamblia* (intestinalis) and *Entamoeba histolytica.*

Although metronidazole is frequently prescribed for the treatment of these infections, it is becoming increasingly ineffective against many parasites currently for reasons unclear. Nitazoxanide has also been described by Rossignol et al as being effective against *Blastocystis hominis* in Egypt—but has never been trialed in USA and appears to be markedly less effective in the US against the US strains. (Rossignol J F et at 2005 *Clin. Gastroenterol. Hepatal.* 3: 987). There appear to be varying *Blastocystis* sensitivities as many patients fail treatment with nitazoxanide as a first line monotherapy in developed countries. *D. fragilis* has been known to be sensitive to Iodoquiriol and doxycycline but alone, this medication are ineffective in the majority of the patients and hence require combination therapies. Indeed, for many parasites monotherapy is becoming ineffective, as has happened with *Helicobacter pylori* where 3-4 antimicrobial agents are now needed combined to achieve eradication.

In one embodiment the present invention relates to a method of treatment using quinolones or fluoroquinolones and related medications for extracellular parasites. These compounds have a similarity to nalidixic acid and several generations of such drugs have been developed including cinoxacin, flumequine, oxolinic acid, piromidic acid, ciprofloxacin, enoxacin, fleroxacin, lomefloxacin, nadifloxacin, norfloxacin, ofloxacin, pefloxacin and rufloxacin. In the next generation are included balofloxacin, grepafloxacin, levofloxacin, pazufloxacin mesilate, sparfloxacin, temafloxacin and tosufloxacin. The latest generation of these includes clinafloxacin, gemifloxacin, moxifloxacin, gatifloxacin, sitafloxacin, trovafloxacin, ecinofloxacin, and prulifloxacin. Fluoroquinolones are known to be active against intracellular parasites (e.g. Rajaa El Bekay et al *Journal of Leukocyte Biology*. 2002; 71:255) but have not been used or described to be useful in treatment of extracellular parasites. Indeed norfloxacin and the other related drugs are known to be effective against bacteria but are reported to be ineffective against viruses, parasites or fungi. The surprising finding from our clinical experience and usage was that this antibacterial agent, norfloxacin, can also be effective in treatment against *Blastocystis hominis*, and *Dientamoeba fragilis*, although it also frequently ineffective as monotherapy and at times it may need to be combined with other medications especially if the parasite infection has previously been treated using other agents. Hence, the method of treatment includes the administration to host of the therapeutically effective amount of norfloxacin or other fluoroquinolones e.g.: levofloxacin or ciprofloxacin [listed above]—from a period of one to fifty days with a dosage of at least one milligram to five grams per day. To improve on the efficacy of the medication a mix of two fluoroquinolones can be used such as norfloxacin and levofloxacin as this appears to enhance and has synergistic effect in the eradication of either *Blastocystis hominis* or *D. fragilis* or both.

The next aspect of the invention relates to the use of combinations of therapies. The quinolone or fluoroquinolones e.g.: norfloxacin can also be combined with tetracycline e.g.: doxycycline to effect better eradication of either *Blastocystis hominis* or *D. fragilis*. The norfloxacin may also be combined also with iodoquinol in those doses mentioned above or with doxycycline. Tetracycline can include any tetracycline including tetracycline itself, chlortetracycline, oxytetracycline, demeclocycline, doxycycline, lymecycline, meclocycline, minocycline, methacycline, rolitetracycline and penimepicycline.

Furthermore, double therapies can include iodoquinol and doxycycline, or nitazoxanide and doxycycline, nitazoxanide and secnidazole, furazolidone and secnidazole, furazolidone and nitazoxanide, or doxycycline and secnidazole and doxycycline and furazolidone and mixtures thereof. Nitazoxanide is one example of the thiazolidone group which can be used here, including others e.g. denitrozoxanide and tizoxanide. Other nitroimidazoles may include metronidazole, secnidazole, tinidazole, ornidazole, as well as furazolidone and others. In one embodiment the combination iodoquinol and doxycycline is excluded.

Double therapies have an advantage and a synergy over single therapies because they block several enzyme systems within the parasite so exacting a greater toll on the infestation. In some circumstances, especially with resistance even triple therapies may need to be combined to effect a cure. Hence, the invention also relates to the composition combining three drugs together. In one embodiment the quinolone or fluoroquinolone may be combined with an azole or imidazole antifungal. In this regard one important synergistic combination is the use norfloxacin and ketoconazole. Other drugs in this group of azoles or imidazole anti-fungals which may be combined with the quinolone or fluoroquinolone include fluconazole, miconazole, clotrimazole, tioconazole, sulconazole, econazole and itraconazole.

These may also be used in conjunction with, other antiparasite drugs in this application, or mixtures thereof, in similar concentrations. Other drugs include emetine, quinacrine, satranidazole, flunidazole and ronidazole.

In another aspect the present invention relates to triple combinations of drugs. In some circumstances, especially with resistance even triple therapies may need to be combined to effect a cure. Hence, the invention also relates to the composition combining three drugs together. For example the use of nitazoxanide, secnidazole and furazolidone or similar triple combinations of the various classes of the drugs listed above. Using this combination even in a recalcitrant difficult to cure *D. fragilis* or *B. hominis* infection eradicates the infection in more than 80% of patients. Again, the treatment requires 1-5 grams/day of each of the omponents from 1-50 days. Other triple combinations can include iodoquinol, furazolidone and nitazoxanide. Combinations can also include diloxinide furoate, doxycycline and metronidazole in various triple combinations.

The invention can be utilized as a treatment given as capsules, enteric coated capsules, or a liquid. In particularly recalcitrant infections especially when the patients have side effects with the oral dosing, one can use an enema of one or more of the drugs used for example, the 3 drugs combined [or other combinations and mixtures of the medications listed above] but in a higher than oral concentration. The enema dosing can range from 1 mg to 30 gm of each drug but the best combination is equivalent to four times the current oral dose given as a single enema or administered through a colonoscope into the terminal ileum or somewhere between the terminal ileum or the anus. This can be given as a single enema or a single infusion through the colonoscope in a volume of 10 ml to 1 liter of liquid, or as recurrent enemas.

The invention will now be described with reference to the following examples which should not be viewed as limiting on the invention.

EXAMPLE 1

A 27 year old female with recurrent IBS-type symptoms characterized by diarrhoea, bloating, flatulence and cramping right iliac fossa pain was colonoscoped and found to have no abnormalities. However on aspiration of colonic fluid during the colonoscopy she was found to have *B. hominis* infection. She was treated with a combination of norfloxacin and ketoconazole. Four weeks after the cessation of the ten day course she continued to be asymptomatic up to four weeks later when a stool test was carried out and beyond. She was found to be cured of *B. hominis* and continued to remain well at 6 months follow up.

EXAMPLE 2

A 16 year old male with intermittent diarrhoea, cramping, abdominal pain and pruritus was found to have *D. fragilis* on stool testing after numerous investigations and visits to the Psychiatrist for treatment of what was diagnosed as anxiety driven IBS. Stool tests found him to be positive for *B. hominis* and he was treated with 400 mg bid of norfloxacin for 14 days. His symptoms abated by about the 20th day and on follow up at 4 weeks he was negative for *B. hominis*. He was negative for *B. hominis* again at 6 months and he was still asymptomatic with negative stool testing.

EXAMPLE 3

A patient was referred after 3 different treatments with metronidazole and tinidazole for a combined *B. hominis* infection and *D. fragilis* infection. Given the previous failed therapies she was given a combination of nitazoxanide, furazolidone, and secnidazole. Her symptoms started abating by week 2. By week 4 her stool tests were normal and her symptoms were virtually gone. It took some time for her symptoms completely to abate but she did not completely lose her pruritus ani. Nevertheless, the *D. fragilis* and *B. hominis* were absent on 4 week and 8 week stool tests.

EXAMPLE 4

A 47 year old patient was referred following various treatments with metronidazole, furazolidone and nitazoxanide for a combination of *B. hominis* and *D. fragilis*. Each time the patient was treated the symptoms improved but then they recurred and the stool examination again showed ongoing *B. hominis* and *D. fragilis*. The patient was brought into the clinic and after bowel preparation a transcolonoscopic infusion of furazolidone, nitazoxanide and secnidazole was carried out. Four weeks later the patient stool tests were negative and the symptoms had abated.

EXAMPLE 5

The patient had previously been treated for resistant *B. hominis* with combination therapies but continued to have stool test positive with symptoms of flatulence, pruritus, ani and abdominal distension continued. The patient was treated with secnidazole 400 mg three times a day, diloxanide furoate 500 mg three times per day and Septrin (cotrimoxazole) double strength DS one tablet twice daily for 10 days. The patient's symptoms progressively abated and the stool tests became negative.

EXAMPLE 6

A 67 year old patient with weight loss and diarrhea presented for an endoscopy. No abnormal findings were found but on histology chronic Giardiasis was found. He was treated by his physician previously on speculative treatment with metronidazole in adequate doses yet the diarrhea did not settle and the patient continued to have *Giardia lamblia* infection found histologically at endoscopy. The patient was treated with metronidazole 400 mg two times a day, together with nitazoxanide 500 mg two times a day and furazolidone 100 mg three times a day and was able to be cleared of infection when next followed up with stool tests. His diarrhea settled.

EXAMPLE 7

The patient had previously failed three drugs combination for treatment of *B. hominis* and *D. fragilis*. The patient was referred to the Clinic for treatment. Symptoms were quite severe and he was given a combination of four medications including Septrin DS (cotrimoxazole) two times a day, diloxanide furoate 500 mg three times a day and secnidazole 400 mg three times a day together with doxycycline 50 mg two times a day. His symptoms resolved in about three weeks although there were quite some major adverse effects with nausea and malaise progressively the patient's symptoms improved two to three months later.

EXAMPLE 8

The patient had quite resistant *Blastocystis hominis* infection and was referred for further treatment following multiple metronidazole failed therapies. He was treated with a rescue therapy containing nitazoxanide 500 mg two times a day, furazolidone 100 mg three times a day, secnidazole 400 mg three times a day and doxycycline 50 mg twice a day for ten days. His symptoms progressively resolved and he was free of the infection on stool test carried out on several occasions at 4 and 6 weeks.

Although the invention has been described with reference to specific examples, it will be appreciated to those skilled in the art that the invention may be embodiment in many other forms.

The invention claimed is:

1. A composition for treating extracellular parasitic infections, the composition comprising:
   (1) one or more of the following combinations:
      (a) an iodoquinol together with a thiazolidone;
      (b) an iodoquinol together with a cotrimoxazole;
      (c) an iodoquinol together with a diloxanide furoate;
      (d) a thiazolidone together with a tetracycline;
      (e) a thiazolidone together with a cotrimoxazole;
      (f) a thiazolidone together with a diloxanide furoate;
      (h) a tetracycline together with a diloxanide furoate;
      (i) a nitroimidazole together with a cotrimoxazole;
      (j) a cotrimoxazole together with a diloxanide furoate;
      (k) at least one quinolone or fluoroquinolone together with an agent selected from the group consisting of a ketoconazole, a miconazole, a clotrimazole, a tioconazole, a sulconazole, a econazole, and a itraconazole; or (1) at least three agents selected from the group consisting of an iodoquinol, a thiazolidone, a nitroimidazole, a cotrimoxazole and a diloxanide furoate; or (2) the composition of (1), further comprising a pharmaceutically acceptable carrier.

2. The composition according to claim 1 wherein the quinolone or fluoroquinolone is one or more compounds selected from the group consisting of cinoxacin, flumequine, oxolinic acid, piromidic acid, ciprofloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin mesilate, sparfloxacin, temafloxacin, tosufloxacin, clinafloxacin, gemifloxacin, moxifloxacin, gatifloxacin, sitafloxacin, trovafloxacin, ecinofloxacin, and prulifloxacin.

3. The composition according to claim 1, wherein the tetracycline is selected from the group consisting of a tetracycline, a chlortetracycline, an oxytetracycline, a demeclocycline, a doxycycline, a lymecycline, a meclocycline, a minocycline, a methacycline, a rolitetracycline and a penimepicycline.

4. The composition of claim 1, further comprising an additional anti-parasitic drug selected from the group consisting of an emetine, a satranidazole, a flunidazole, a ronidazole and mixtures thereof.

5. The composition of claim 1, wherein the thiazolidone is selected from the group consisting of a nitazoxanide, a denitrozoxanide, a tizoxanide and mixtures thereof.

6. The composition of claim 1, wherein the nitroimidazole is selected from the group consisting of a metronidazole, a etronidazole, a secnidazole, an ornidazole, a furazolidone and mixtures thereof.

7. The composition of claim 1, wherein the composition comprises the combination of a norfloxacin and a ketoconazole.

8. The composition according to claim 1 wherein the composition includes two agents selected from the group consisting of a nitazoxanide and a doxycycline, a nitazoxanide and a secnidazole, a furazolidone and a secnidazole, a furazolidone and a nitazoxanide, a doxycycline and a secnidazole, and a doxycycline and a furazolidone, and mixtures thereof.

9. A method for treating extracellular parasitic infections in a vertebrate in need of said treatment,
wherein said treatment comprises administering to said vertebrate a therapeutically effective amount of a composition of claim 1.

10. The method of claim 9 wherein the extracellular parasite is *Blastocysts hominis, Dientamoeba fragilis* or both.

11. The method of claim 9, wherein the extracellular parasite is a *Giardia lamblia* (intestinalis) or an *Entamoeba histolytica*.

12. The method of claim 9, wherein the composition or combination is administered via a colonoscope, or as a transcolonoscopic infusion.

13. The method of claim 9, wherein the composition or combination is formulated as a capsule, an enteric coated capsule or a liquid.

14. The method of claim 9, wherein the composition or combination is administered as a single enema or a single infusion or as recurrent enemas through a colonoscope in a volume of 10 ml to 1 liter of liquid.

15. The composition of claim 1, wherein the composition is formulated as a capsule, an enteric coated capsule or a liquid.

16. The composition of claim 1, wherein the composition comprises one or more of the following combinations: at least two agents selected from the group consisting of a thiazolidone, a tetracycline, a nitroimidazole, a cotrimoxazole and a diloxanide furoate.

17. The composition of claim 1, wherein the composition comprises an iodoquinol together with a thiazolidone.

18. The composition of claim 1, wherein the composition comprises an iodoquinol together with a cotrimoxazole.

19. The composition of claim 1, wherein the composition comprises an iodoquinol together with a diloxanide furoate.

20. The composition of claim 1, wherein the composition comprises a thiazolidone together with a tetracycline.

21. The composition of claim 1, wherein the composition comprises a thiazolidone together with a cotrimoxazole.

22. The composition of claim 1, wherein the composition comprises a thiazolidone together with a diloxanide furoate.

23. The method of claim 9 wherein said treatment comprises administering to the vertebrate a therapeutically effective amount of a composition that comprises a tetracycline together with a nitroimidazole.

24. The composition of claim 1, wherein the composition comprises a tetracycline together with a diloxanide furoate.

25. The composition of claim 1, wherein the composition comprises a nitroimidazole together with a cotrimoxazole.

26. The composition of claim 1, wherein the composition comprises a cotrimoxazole together with a diloxanide furoate.

27. The composition of claim 1, wherein the composition comprises at least one quinolone or fluoroquinolone together with an agent selected from the group consisting of: a ketoconazole, a miconazole, a clotrimazole, a tioconazole, a sulconazole, a econazole, and an itraconazole.

28. The composition of claim 1, wherein the composition comprises at least three agents selected from the group consisting of an iodoquinol, a thiazolidone, a nitroimidazole, a cotrimoxazole and a diloxanide furoate.

29. The composition of claim 1, wherein the composition comprises the combination of a nitazoxanide, a furzolidone and a secnidazole.

30. The composition of claim 1, wherein the composition comprises the combination of an iodoquinol, a furazolidone and a nitazoxanide.

31. The composition of claim 1, wherein the composition comprises the combination of a diloxanide furoate, a doxycycline and a metronidazole.

32. The composition of claim 1, wherein the composition comprises the combination of a secnidazole, a diloxanide furoate and a cotrimoxazole.

33. The composition of claim 1, wherein the composition comprises the combination of a metronidazole, a nitazoxanide and a furazolidone.

34. The composition of claim 1, wherein the composition comprises the combination of a cotrimoxazole, a diloxanide furoate, a secnidazole and a doxycycline.

35. The composition of claim 1, wherein the composition comprises the combination of a nitazoxanide, a furazolidone, a secnidazole and a doxycycline.

* * * * *

UNITED STATES PATENT AND TRADEMARK OFFICE
CERTIFICATE OF CORRECTION

| | |
|---|---|
| PATENT NO. | : 8,999,360 B2 |
| APPLICATION NO. | : 13/502366 |
| DATED | : April 7, 2015 |
| INVENTOR(S) | : Thomas Julius Borody |

It is certified that error appears in the above-identified patent and that said Letters Patent is hereby corrected as shown below:

On the Title Page

Under item (12), "Borody et al." should read --Borody--

Item (76), Line 2, remove Soledad Carsula, Rouse Hill (AU)

Signed and Sealed this
Fourteenth Day of February, 2023

Katherine Kelly Vidal
*Director of the United States Patent and Trademark Office*